(12) United States Patent
Cohen (10) Patent No.: US 10,488,480 B2
(45) Date of Patent: Nov. 26, 2019

(54) SYSTEM AND METHOD FOR ADAPTIVE DICTIONARY MATCHING IN MAGNETIC RESONANCE FINGERPRINTING

(71) Applicant: THE GENERAL HOSPITAL CORPORATION, Boston, MA (US)

(72) Inventor: Ouri Cohen, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 374 days.

(21) Appl. No.: 15/116,999

(22) PCT Filed: Jan. 20, 2015

(86) PCT No.: PCT/US2015/011948
§ 371 (c)(1),
(2) Date: Aug. 5, 2016

(87) PCT Pub. No.: WO2015/160400
PCT Pub. Date: Oct. 22, 2015

(65) Prior Publication Data
US 2016/0349341 A1 Dec. 1, 2016

Related U.S. Application Data

(60) Provisional application No. 61/938,288, filed on Feb. 11, 2014, provisional application No. 61/938,300, (Continued)

(51) Int. Cl.
*G01R 33/54* (2006.01)
*A61B 5/00* (2006.01)
(Continued)

(52) U.S. Cl.
CPC ............ *G01R 33/543* (2013.01); *A61B 5/055* (2013.01); *A61B 5/0555* (2013.01);
(Continued)

(58) Field of Classification Search
CPC ......... A61B 5/05; A61B 5/055; A61B 5/0555; A61B 5/7271; A61B 5/7282; G01R 33/44;
(Continued)

(56) References Cited

U.S. PATENT DOCUMENTS 6,348,918 B1 2/2002 Szeliski et al.
6,700,374 B1 3/2004 Wu et al.
(Continued)

FOREIGN PATENT DOCUMENTS

WO WO2013/010080 A1 1/2013

OTHER PUBLICATIONS

Labadie et al., "Rapid Metabolite Mapping with Exocycled SCEPSIS," Max Planck Institute Research Report 2010/2011. p. 255.
(Continued)

*Primary Examiner* — Huy Q Phan
*Assistant Examiner* — David B Frederiksen
(74) *Attorney, Agent, or Firm* — Quarles & Brady LLP (57) ABSTRACT

Systems and methods for estimating quantitative parameters of a subject from data acquired using a magnetic resonance imaging (MRI) system. MR data acquired with an MRI system is provided, which represents a plurality of different signal evolutions acquired using different acquisition parameter settings. An initial dictionary comprising a plurality of signal templates is generated that coarsely sample acquisition parameters used when acquiring the provided MR data. The MR data is compared with the initial dictionary. The quantitative parameters associated with an entry in the initial dictionary are stored as the estimated quantitative parameters when the comparison satisfies a threshold criterion and the initial dictionary is updated when the comparison does not satisfy the threshold criterion.

16 Claims, 3 Drawing Sheets

Related U.S. Application Data filed on Feb. 11, 2014, provisional application No. 62/025,268, filed on Jul. 16, 2014.

(51) Int. Cl.
  *A61B 5/055* (2006.01)
  *G01R 33/48* (2006.01)
  *G01R 33/50* (2006.01)

(52) U.S. Cl.
  CPC ........ *A61B 5/7282* (2013.01); *G01R 33/4828* (2013.01); *G01R 33/50* (2013.01)

(58) Field of Classification Search
  CPC .. G01R 33/48; G01R 33/482; G01R 33/4828; G01R 33/50; G01R 33/54; G01R 33/543; G01R 33/546; G01R 33/56
  See application file for complete search history.

(56) References Cited

U.S. PATENT DOCUMENTS

| | | | |
|---|---|---|---|
| 7,337,205 B2 | 2/2008 | Sazegari | |
| 7,772,844 B2 | 8/2010 | Hurd | |
| 7,848,797 B2 | 12/2010 | Kong et al. | |
| 7,945,305 B2 | 5/2011 | Aggarwal et al. | |
| 8,558,546 B2 | 10/2013 | Griswold et al. | |
| 8,723,518 B2 | 5/2014 | Seiberlich et al. | |
| 2012/0235678 A1 | 9/2012 | Seibelich et al. | |
| 2012/0296193 A1* | 11/2012 | Koktzoglou | A61B 5/02007 600/410 |
| 2013/0265047 A1 | 10/2013 | Griswold et al. | |
| 2013/0265050 A1* | 10/2013 | Grodzki | G01R 33/4806 324/309 |
| 2013/0271132 A1* | 10/2013 | Griswold | G01R 33/5612 324/309 |
| 2013/0278255 A1* | 10/2013 | Khalighi | G01R 33/246 324/309 |
| 2014/0055133 A1* | 2/2014 | I | G01R 33/28 324/309 |
| 2014/0103924 A1* | 4/2014 | Griswold | G01R 33/3635 324/309 |
| 2014/0167754 A1* | 6/2014 | Jerecic | G01R 33/561 324/309 |
| 2014/0266204 A1* | 9/2014 | Watanabe | A61B 5/055 324/318 |
| 2014/0292328 A1* | 10/2014 | Brady-Kalnay | G01R 33/3614 324/309 |
| 2015/0070012 A1* | 3/2015 | Griswold | G01R 33/283 324/309 |
| 2015/0186606 A1* | 7/2015 | Kuang | A61B 5/055 702/19 |

OTHER PUBLICATIONS

Ma et al., Nature 2013; 495:187-192.
Wang, et al., MRF Denoising with Compressed Sensing and Adaptive Filtering, In Biomedical Imaging (ISBI), 2014 IEEE 11th International Symposium on, pp. 870-873.
European Patent Office, Partial Supplementary European Search Report, Application No. 15779449.6, dated Jan. 4, 2018, 15 pages.
International Search Report and Written Opinion for PCT/US2015/011948, dated Oct. 1, 2015.

\* cited by examiner

SYSTEM AND METHOD FOR ADAPTIVE DICTIONARY MATCHING IN MAGNETIC RESONANCE FINGERPRINTING

CROSS-REFERENCE TO RELATED APPLICATIONS

This application represents the U.S. National Stage of International Application No. PCT/US2015/011948, filed Jan. 20, 2015 which is based on, claims priority to, and incorporates herein by reference in its entirety U.S. Provisional Patent Application Ser. No. 61/938,288, filed Feb. 11, 2014 and entitled "Magnetic Resonance Fingerprinting Adaptive Dictionary Creation and Matching"; is based on, claims priority to, and incorporates herein by reference in its entirety U.S. Provisional Patent Application Ser. No. 61/938, 300, filed Feb. 11, 2014, and entitled "Accelerated and Optimized MR Fingerprinting"; and is based on, claims priority to, and incorporates herein by reference in its entirety U.S. Provisional Patent Application Ser. No. 62/025, 268, filed Jul. 16, 2014, and entitled "System and Method for Adaptive Dictionary Matching in Magnetic Resonance Fingerprinting."

STATEMENT REGARDING FEDERALLY SPONSORED RESEARCH

This invention was made with government support under W81XWH-09-2-001 awarded by the Department of Defense. The government has certain rights in the invention.

BACKGROUND

The present disclosure relates to systems and methods for magnetic resonance imaging ("MRI"). More particularly, the disclosure relates to systems and methods for producing quantitative parameter maps using magnetic resonance fingerprinting ("MRF").

MRF is an imaging technique that enables quantitative mapping of tissue or other material properties based on random or pseudorandom measurements of the subject or object being imaged. Examples of parameters that can be mapped include longitudinal relaxation time, $T_1$; transverse relaxation time, $T_2$; main magnetic field map, $B_0$; and proton density, $\rho$. MRF is generally described in U.S. Pat. No. 8,723,518, which is herein incorporated by reference in its entirety.

The random or pseudorandom measurements obtained in MRF techniques are achieved by varying the acquisition parameters from one repetition time ("TR") period to the next, which creates a time series of images with varying contrast. Examples of acquisition parameters that can be varied include flip angle, radio frequency ("RF") pulse phase, TR, echo time ("TE"), and sampling patterns, such as by modifying one or more readout encoding gradients.

The data acquired with MRF techniques are compared with a dictionary of signal models, or templates, that have been generated for different acquisition parameters from magnetic resonance signal models, such as Bloch equation-based physics simulations. This comparison allows estimation of the desired physical parameters, such as those mentioned above. The parameters for the tissue or other material in a given voxel are estimated to be the values that provide the best signal template matching.

Quantitative parameters are estimated in MRF by matching acquired signals with pre-computed signals that are stored in a dictionary of tissue parameters. To ensure that a correct match is found for each acquired signal, the dictionary must cover a large range of tissue parameters and must have a fine resolution. These two requirements result in dictionaries that are large (e.g., on the order of one million entries). As a consequence of the large dictionary size, significant processing time is required to match acquired signals to the dictionary, and large storage space is needed to store the dictionaries.

Thus, there remains a need to provide systems and methods for MRF that are more computationally efficient, and have reduced data storage requirements.

SUMMARY OF THE INVENTION

The present invention overcomes the aforementioned drawbacks by providing a system and method for estimating quantitative parameters of a subject using a magnetic resonance imaging ("MRI") system using a dictionary. More particularly, the dictionary may include a plurality of signal templates that coarsely sample acquisition parameters used when acquiring data. The acquired data is compared with the dictionary. The quantitative parameters associated with an entry in the dictionary are stored as the estimated quantitative parameters when the comparison satisfies a threshold criterion. As such, systems and methods are provided that are more computationally efficient, and have reduced data storage requirements.

In accordance with one aspect of the disclosure, a method is provided for estimating quantitative parameters of a subject using a magnetic resonance imaging (MRI) system. The method includes providing MR data acquired with an MRI system, the acquired MR data representing a plurality of different signal evolutions acquired using different acquisition parameter settings and generating an initial dictionary comprising a plurality of signal templates that coarsely sample acquisition parameters used when acquiring the provided MR data. The method also includes comparing the provided MR data with the initial dictionary and storing the quantitative parameters associated with an entry in the initial dictionary as the estimated quantitative parameters when the comparison satisfies a threshold criterion. The method further includes updating the initial dictionary when the comparison does not satisfy the threshold criterion, and repeating the process using the updated dictionary.

In accordance with another aspect of the disclosure, a method is provided for estimating quantitative parameters of a subject using a magnetic resonance imaging (MRI) system. The method includes providing MR data acquired with an MRI system, the provided MR data representing a plurality of different signal evolutions acquired using different acquisition parameter settings and generating an initial dictionary comprising a plurality of signal templates that coarsely sample acquisition parameters used when acquiring the provided MR data. The method also includes comparing the provided MR data with the initial dictionary and storing the quantitative parameters associated with an entry in the initial dictionary as the estimated quantitative parameters when the comparison satisfies a threshold criterion. The method further includes updating the threshold criterion when the comparison does not satisfy the threshold criterion, and repeating the process using the updated threshold criterion.

In accordance with yet another aspect of the disclosure, a magnetic resonance imaging (MRI) system is provided that includes a magnet system configured to generate a polarizing magnetic field about at least a portion of a subject arranged in the MRI system. The MRI system also includes a magnetic gradient system including a plurality of magnetic gradient coils configured to apply at least one magnetic gradient field to the polarizing magnetic field and a radio frequency (RF) system configured to apply an RF field to the subject and to receive magnetic resonance signals from the subject using a coil array. The MRI system also includes a computer system programmed to control the magnetic gradient system and RF system to acquire MR data from the subject using different acquisition parameter settings and representing a plurality of different signal evolutions and generate an initial dictionary comprising a plurality of signal templates that coarsely sample acquisition parameters used when acquiring the MR data. The computer system is further programmed to compare the MR data with the initial dictionary, store the quantitative parameters associated with an entry in the initial dictionary as the estimated quantitative parameters when the comparison satisfies a threshold criterion, update the initial dictionary when the comparison does not satisfy the threshold criterion, and repeat the process using the updated dictionary. The computer system is further configured to generate a quantitative parameter map of the subject using the estimated quantitative parameters.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here are systems and methods for estimating quantitative parameters with magnetic resonance fingerprinting ("MRF"), in which acquired signal vectors are matched with a dictionary that may be, for example, efficiently used and adaptively generated.

In general, MRF techniques utilize a data acquisition scheme that causes signals from different materials or tissues to be spatially and temporally incoherent by continuously varying acquisition parameters throughout the data acquisition process. Examples of acquisition parameters that can be varied include flip angle, radio frequency ("RF") pulse phase, repetition time ("TR"), echo time ("TE"), sampling patterns, such as by modifying readout encoding gradients, and the like. Preferably, the acquisition parameters are varied in a pseudorandom manner. As a result of the spatial and temporal incoherence imparted by the this acquisition scheme, each material or tissue is associated with a unique signal evolution or "fingerprint," that is a function of multiple different physical parameters, including longitudinal relaxation time, $T_1$; transverse relaxation time, $T_2$; main magnetic field map, $B_0$; and proton density, $\rho$.

Quantitative parameter maps can be generated from these acquired signals based on a comparison of the signals to a predefined dictionary of predicted signal evolutions. Each of these dictionaries is associated with different combinations of material, environmental, and acquisition parameters. As an example, the comparison of the acquired signals to a dictionary can be performed using any suitable matching or pattern recognition technique. This comparison results in the selection of a signal vector, which may constitute a weighted combination of signal vectors, from the dictionary that best correspond to the observed signal evolution. The selected signal vector includes values for multiple different quantitative parameters, which can be extracted from the selected signal vector and used to generate the relevant quantitative parameter maps.

As described above, quantitative parameters can be estimated in MRF by matching acquired signals with precomputed signals that are stored in a relatively large dictionary of tissue parameters. This matching can require significant processing time to match acquired signals to the large dictionary, and large storage space is needed to store the dictionaries. Additionally, the range of the tissue parameters needed in a dictionary can be imprecise based on different pathological conditions, and can also be subject dependent. As a consequence, a new dictionary often needs to be generated to cover those cases where the acquired signals correspond to tissue parameters outside of the range covered by the currently available dictionary. The systems and methods of the present invention overcome these drawbacks by generating smaller dictionaries that are more computationally manageable, and that are specifically tailored to the acquired data.

Figure 1:
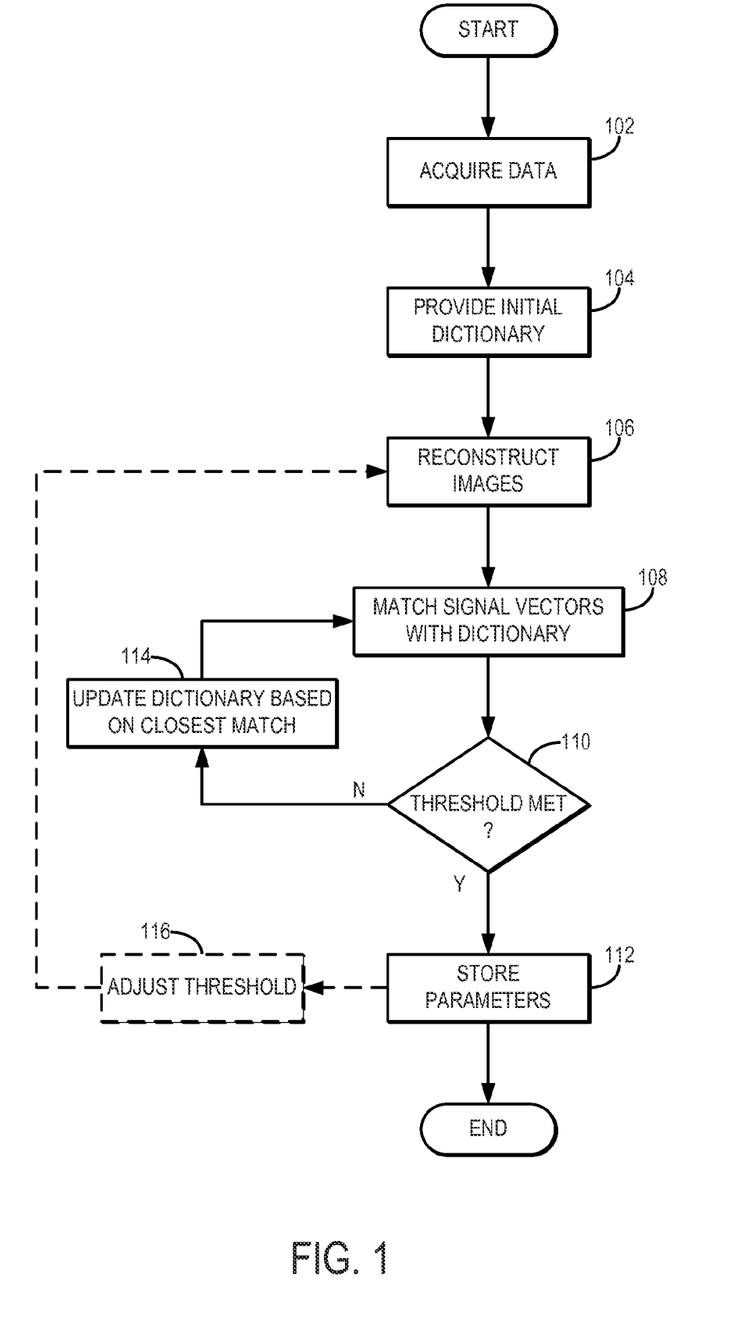
FIG. 1 is a flowchart setting forth the steps of an example method for performing magnetic resonance fingerprinting ("MRF") using an adaptively updated dictionary.

Referring now to FIG. 1, a flowchart is provided that sets forth the steps of an example method for estimating quantitative parameters using MRF techniques and an adaptively generated dictionary. The method includes acquiring or otherwise providing data, as indicated at step 102. For instance, data are acquired with an MRI system performing a suitable MRF data acquisition. As another example, data can be provided, such as by retrieving previously acquired data from a suitable storage medium.

After data are acquired or otherwise provided, an initial dictionary may be generated, as indicated at step 104. To do so, a parameter range is selected. For example, the parameter range may have limits well above and below those expected in vivo. In any case, vector trajectories may be computed over the parameter range and, stored in a matrix, A. To do so, this initial dictionary may coarsely samples the acquisition parameters used when acquiring the provided data.

From the acquired or otherwise provided data, images are reconstructed at step 106. These images may then be processed on a voxel-by-voxel basis based on the initial dictionary, as indicated at step 108. For instance, a signal vector formed as the concatenation of acquired signals for a given voxel location is compared to entries in the initial dictionary. As one example, the comparison is based on a dot product between a given signal vector and each entry in the initial dictionary. Because the initial dictionary is significantly smaller than the conventional dictionaries used in MRF, this initial matching can be performed quickly and with a significantly reduced computational and data storage burden.

The comparison can be quantified by a numerical similarity measure, which can be checked against a threshold value to assess the similarity between a given signal vector and entry in the initial dictionary, as indicated at decision block 110. For instance, when a similarity measure is at or above a certain threshold value, the voxel associated with the signal vector can be assigned the parameters in the initial dictionary entry that was matched with the signal vector, as indicated at step 112.

If, for a given signal vector, none of the entries in the initial dictionary closely match the signal vector (i.e., the similarity measure is below the threshold value) the initial dictionary is updated using an adaptive routine, as indicated at step 114. For instance, the closest match in the initial dictionary is used to initialize a global optimization routine that searches the allowed parameter space for a better match. The parameter trajectories generated based on this optimum search may be reinserted into the dictionary to facilitate and speed up the matching of subsequent voxels.

In some embodiments, the adaptive routine can include iteratively updating the threshold value rather than adaptively modifying the initial dictionary. For instance, at optional process block 116, a higher or lower threshold can be used in subsequent iterations. In this regard, the process reiterates to process block 106 as the current dictionary entries can serve as the seed points for each subsequently-adjusted threshold. As such, it is possible to achieve desired precision in the match obtained and adjust the desired precision. For example, the current dictionary can be iteratively refined by iterating, as described, with the current dictionary entries as the seed points and using a repeatedly higher threshold.

The systems and methods of the present invention are thus capable of yielding smaller dictionaries for use in MRF applications. Moreover, the dictionaries may be specifically adapted to the acquired data, resulting in better matching. Because the dictionaries are generated based on the acquired data, it is not necessary to acquire foreknowledge or rely on a priori calculations of the tissue parameters.

Figure 2:
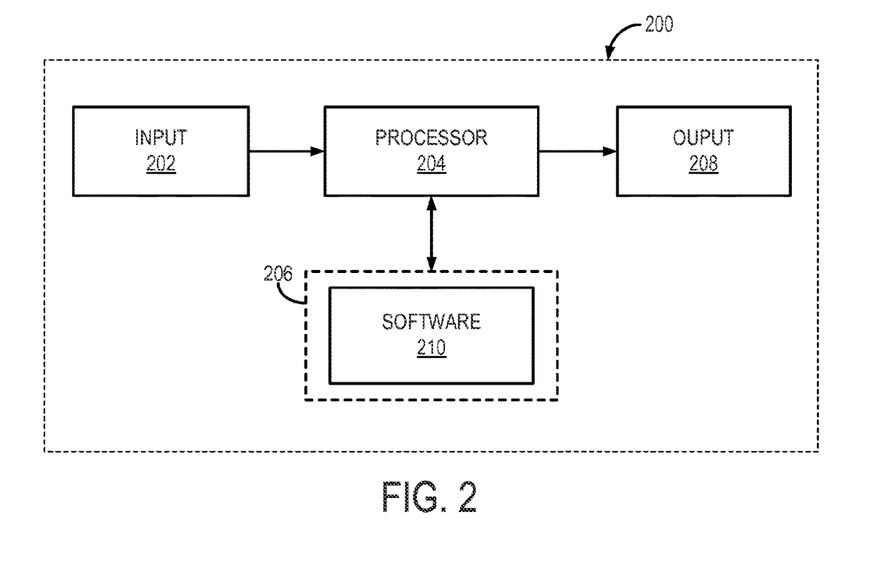
FIG. 2 is a block diagram of an example computer system that can implement some embodiments of the present invention.

Referring now to FIG. 2, a block diagram is illustrated of an example computer system 200 that can be used for producing an iteratively updated dictionary and for implementing an adaptive matching algorithm in accordance with some embodiments of the present invention. The system 200 generally may include an input 202, at least one processor 204, a memory 206, and an output 208. The system 200 may be, for example, a workstation, a notebook computer, a personal digital assistant ("PDA"), a multimedia device, a network server, a mainframe, or any other general-purpose or application-specific computing device. In some embodiments, the computer system 200 may form a part of a magnetic resonance imaging ("MRI") system, as will be described. The computer system 200 may operate autonomously or semi-autonomously, or may read executable software instructions from a computer-readable medium (such as a hard drive, a CD-ROM, flash memory, and the like), or may receive instructions from a user, or any another source logically connected to a computer or device, such as another networked computer or server, via the input 202.

The input 202 may take any shape or form, as desired, for operation of the computer system 200, including the ability for selecting, entering, or otherwise specifying parameters consistent with operating the computer system 200. In some instances, the input 202 may be designed to receive data acquired with an MRI system, which may be in the form of reconstructed images or raw k-space data.

Among the processing tasks for operating the computer system 200, the at least one processor 204 may be configured to perform the method described above with respect to FIG. 1.

The memory 206 may contain software 208, and may be configured for storage and retrieval of processed information and data to be processed by the processor 204. In some aspects, the software 208 may contain instructions directed to performing the method described above with respect to FIG. 1.

Figure 3:
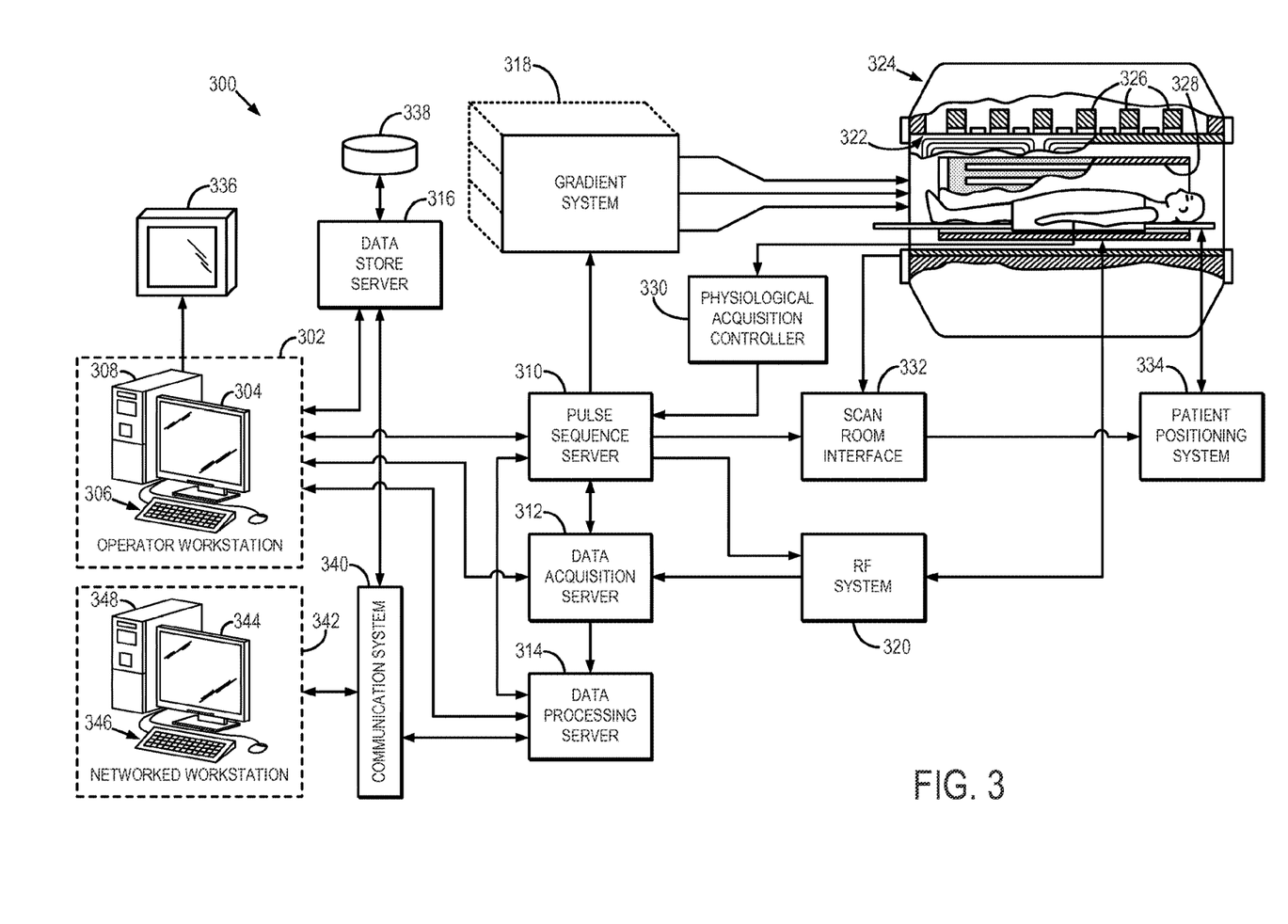
FIG. 3 is a block diagram of an example of a magnetic resonance imaging ("MRI") system.

Referring particularly now to FIG. 3, an example of a magnetic resonance imaging ("MRI") system 300 is illustrated. The MRI system 300 includes an operator workstation 302, which will typically include a display 304; one or more input devices 306, such as a keyboard and mouse; and a processor 308. The processor 308 may include a commercially available programmable machine running a commercially available operating system. The operator workstation 302 provides the operator interface that enables scan prescriptions to be entered into the MRI system 300. In general, the operator workstation 302 may be coupled to four servers: a pulse sequence server 310; a data acquisition server 312; a data processing server 314; and a data store server 316. The operator workstation 302 and each server 310, 312, 314, and 316 are connected to communicate with each other. For example, the servers 310, 312, 314, and 316 may be connected via a communication system 340, which may include any suitable network connection, whether wired, wireless, or a combination of both. As an example, the communication system 340 may include both proprietary or dedicated networks, as well as open networks, such as the internet.

The pulse sequence server 310 functions in response to instructions downloaded from the operator workstation 302 to operate a gradient system 318 and a radiofrequency ("RF") system 320. Gradient waveforms necessary to perform the prescribed scan are produced and applied to the gradient system 318, which excites gradient coils in an assembly 322 to produce the magnetic field gradients $G_x$, $G_y$, and $G_z$ used for position encoding magnetic resonance signals. The gradient coil assembly 322 forms part of a magnet assembly 324 that includes a polarizing magnet 326 and a whole-body RF coil 328.

RF waveforms are applied by the RF system 320 to the RF coil 328, or a separate local coil (not shown in FIG. 3), in order to perform the prescribed magnetic resonance pulse sequence. Responsive magnetic resonance signals detected by the RF coil 328, or a separate local coil (not shown in FIG. 3), are received by the RF system 320, where they are amplified, demodulated, filtered, and digitized under direction of commands produced by the pulse sequence server 310. The RF system 320 includes an RF transmitter for producing a wide variety of RF pulses used in MRI pulse sequences. The RF transmitter is responsive to the scan prescription and direction from the pulse sequence server 310 to produce RF pulses of the desired frequency, phase, and pulse amplitude waveform. The generated RF pulses may be applied to the whole-body RF coil 328 or to one or more local coils or coil arrays (not shown in FIG. 3).

The RF system 320 also includes one or more RF receiver channels. Each RF receiver channel includes an RF preamplifier that amplifies the magnetic resonance signal received by the coil 328 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \qquad (1);$$

and the phase of the received magnetic resonance signal may also be determined according to the following relationship:

$$\varphi = \tan^{-1}\left(\frac{Q}{I}\right). \quad (2)$$

The pulse sequence server 310 also optionally receives patient data from a physiological acquisition controller 330. By way of example, the physiological acquisition controller 330 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 310 to synchronize, or "gate," the performance of the scan with the subject's heart beat or respiration.

The pulse sequence server 310 also connects to a scan room interface circuit 332 that receives signals from various sensors associated with the condition of the patient and the magnet system. It is also through the scan room interface circuit 332 that a patient positioning system 334 receives commands to move the patient to desired positions during the scan.

The digitized magnetic resonance signal samples produced by the RF system 320 are received by the data acquisition server 312. The data acquisition server 312 operates in response to instructions downloaded from the operator workstation 302 to receive the real-time magnetic resonance data and provide buffer storage, such that no data is lost by data overrun. In some scans, the data acquisition server 312 does little more than pass the acquired magnetic resonance data to the data processor server 314. However, in scans that require information derived from acquired magnetic resonance data to control the further performance of the scan, the data acquisition server 312 is programmed to produce such information and convey it to the pulse sequence server 310. For example, during prescans, magnetic resonance data is acquired and used to calibrate the pulse sequence performed by the pulse sequence server 310. As another example, navigator signals may be acquired and used to adjust the operating parameters of the RF system 320 or the gradient system 318, or to control the view order in which k-space is sampled. In still another example, the data acquisition server 312 may also be employed to process magnetic resonance signals used to detect the arrival of a contrast agent in a magnetic resonance angiography ("MRA") scan. By way of example, the data acquisition server 312 acquires magnetic resonance data and processes it in real-time to produce information that is used to control the scan.

The data processing server 314 receives magnetic resonance data from the data acquisition server 312 and processes it in accordance with instructions downloaded from the operator workstation 302. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 314 are conveyed back to the operator workstation 302 where they are stored. Real-time images are stored in a data base memory cache (not shown in FIG. 3), from which they may be output to operator display 312 or a display 336 that is located near the magnet assembly 324 for use by attending physicians. Batch mode images or selected real time images are stored in a host database on disc storage 338. When such images have been reconstructed and transferred to storage, the data processing server 314 notifies the data store server 316 on the operator workstation 302. The operator workstation 302 may be used by an operator to archive the images, produce films, or send the images via a network to other facilities.

The MRI system 300 may also include one or more networked workstations 342. By way of example, a networked workstation 342 may include a display 344; one or more input devices 346, such as a keyboard and mouse; and a processor 348. The networked workstation 342 may be located within the same facility as the operator workstation 302, or in a different facility, such as a different healthcare institution or clinic.

The networked workstation 342, whether within the same facility or in a different facility as the operator workstation 302, may gain remote access to the data processing server 314 or data store server 316 via the communication system 340. Accordingly, multiple networked workstations 342 may have access to the data processing server 314 and the data store server 316. In this manner, magnetic resonance data, reconstructed images, or other data may be exchanged between the data processing server 314 or the data store server 316 and the networked workstations 342, such that the data or images may be remotely processed by a networked workstation 342. This data may be exchanged in any suitable format, such as in accordance with the transmission control protocol ("TCP"), the internet protocol ("IP"), or other known or suitable protocols.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for estimating quantitative parameters of a subject using a magnetic resonance imaging (MRI) system, the steps of the method comprising:
   (a) providing MR data acquired with the MRI system, the acquired MR data representing a plurality of different signal evolutions acquired using different acquisition parameter settings;
   (b) generating an initial dictionary comprising a plurality of signal templates that coarsely sample acquisition parameters used when acquiring the provided MR data;
   (c) comparing the provided MR data with the initial dictionary and:
      (i) storing the quantitative parameters associated with an entry in the initial dictionary as the estimated quantitative parameters when the comparison satisfies a threshold criterion; and
      (ii) updating the initial dictionary when the comparison does not satisfy the threshold criterion, and wherein step (c) is repeated using the updated dictionary, wherein updating the initial dictionary includes performing a global optimization that searches a parameter space encompassing potential quantitative parameters, and added entries to the initial dictionary based on the global optimization.

2. The method as recited in claim 1, wherein performing the global optimization includes identifying a seed entry based on the comparison performed in step (c).

3. The method as recited in claim 2, wherein the seed entry is identified as an entry in the initial dictionary that when compared to the provided MR data yields a similarity value closest to the threshold criterion.

4. The method as recited in claim 1, further comprising generating a quantitative parameter map using the estimated quantitative parameters.

5. The method as recited in claim 1, wherein the different acquisition parameter settings includes at least one of an echo time, a repetition time, a flip angle, a radio frequency (RF) pulse phase, or a k-space sampling pattern.

6. The method as recited in claim 1, wherein the quantitative parameters include at least one of a longitudinal relaxation time, a transverse relaxation time, a longitudinal magnetization, a field map, or a proton density.

7. A method for estimating quantitative parameters of a subject using a magnetic resonance imaging (MRI) system, the steps of the method comprising:
   (a) providing MR data acquired with the MRI system, the provided MR data representing a plurality of different signal evolutions acquired using different acquisition parameter settings;
   (b) generating an initial dictionary comprising a plurality of signal templates that coarsely sample acquisition parameters used when acquiring the provided MR data;
   (c) comparing the provided MR data with the initial dictionary and:
      (i) storing the quantitative parameters associated with an entry in the initial dictionary as the estimated quantitative parameters when the comparison satisfies a threshold criterion; and
      (ii) updating the threshold criterion when the comparison does not satisfy the threshold criterion, and wherein step (c) is repeated using the updated threshold criterion
         wherein updating the initial dictionary includes performing a global optimization that searches a parameter space encompassing potential quantitative parameters and uses entries in the initial dictionary as seed entries for new entries based on the global optimization.

8. The method as recited in claim 7, wherein the seed entries are identified as an entries in the initial dictionary that, when compared to the provided MR data, yield a similarity value within the updated threshold criterion.

9. The method as recited in claim 7, further comprising generating a quantitative parameter map using the estimated quantitative parameters.

10. The method as recited in claim 7, wherein the different acquisition parameter settings includes at least one of an echo time, a repetition time, a flip angle, a radio frequency (RF) pulse phase, or a k-space sampling pattern.

11. The method as recited in claim 7, wherein the quantitative parameters include at least one of a longitudinal relaxation time, a transverse relaxation time, a longitudinal magnetization, a field map, or a proton density.

12. A magnetic resonance imaging (MRI) system, comprising:
   a magnet system configured to generate a polarizing magnetic field about at least a portion of a subject arranged in the MM system;
   a magnetic gradient system including a plurality of magnetic gradient coils configured to apply at least one magnetic gradient field to the polarizing magnetic field;
   a radio frequency (RF) system configured to apply an RF field to the subject and to receive magnetic resonance signals from the subject using a coil array;
   a computer system programmed to:
      (a) control the magnetic gradient system and RF system to acquire MR data from the subject using different acquisition parameter settings and representing a plurality of different signal evolutions;
      (b) generate an initial dictionary comprising a plurality of signal templates that coarsely sample acquisition parameters used when acquiring the MR data;
      (c) compare the MR data with the initial dictionary and:
         (i) store the quantitative parameters associated with an entry in the initial dictionary as the estimated quantitative parameters when the comparison satisfies a threshold criterion;
         (ii) update the initial dictionary when the comparison does not satisfy the threshold criterion, and wherein step (c) is repeated using the updated dictionary by performing a global optimization that searches a parameter space encompassing potential quantitative parameters, and add entries to the initial dictionary based on the global optimization to update the initial dictionary; and
      (d) generate a quantitative parameter map of the subject using the estimated quantitative parameters.

13. The system as recited in claim 12, wherein the computer system is further configured to identify a seed entry based on the comparison performed in step (c) to perform the global optimization.

14. The system as recited in claim 13, wherein the computer system is further configured to identify the seed entry as an entry in the initial dictionary that, when compared to the MR data, yields a similarity value closest to the threshold criterion.

15. The system as recited in claim 12, wherein the different acquisition parameter settings includes at least one of an echo time, a repetition time, a flip angle, a radio frequency (RF) pulse phase, or a k-space sampling pattern.

16. The system as recited in claim 12, wherein the quantitative parameters include at least one of a longitudinal relaxation time, a transverse relaxation time, a longitudinal magnetization, a field map, or a proton density.

* * * * *

UNITED STATES PATENT AND TRADEMARK OFFICE
CERTIFICATE OF CORRECTION

PATENT NO. : 10,488,480 B2  
APPLICATION NO. : 15/116999  
DATED : November 26, 2019  
INVENTOR(S) : Ouri Cohen Page 1 of 1

It is certified that error appears in the above-identified patent and that said Letters Patent is hereby corrected as shown below:

In the Claims

Column 9, Claim 7, Line 40, "initial dictionary" should be --threshold criterion--.

Column 10, Claim 12, Line 9, "MM" should be --MRI--.

Signed and Sealed this  
Seventh Day of January, 2020

Andrei Iancu  
*Director of the United States Patent and Trademark Office*